(12) United States Patent
Steed et al.

(10) Patent No.: US 8,313,764 B2
(45) Date of Patent: *Nov. 20, 2012

(54) WOUND HEALING DEVICE

(75) Inventors: David L. Steed, Pittsburgh, PA (US); Linda O. Palladino, Stormville, NY (US)

(73) Assignee: Stemnion, Inc., Pittsburgh, PA (US)

( * ) Notice: Subject to any disclaimer, the term of this patent is extended or adjusted under 35 U.S.C. 154(b) by 46 days.

This patent is subject to a terminal disclaimer.

(21) Appl. No.: 13/134,881

(22) Filed: Jun. 20, 2011

(65) Prior Publication Data

US 2011/0311609 A1     Dec. 22, 2011

Related U.S. Application Data

(60) Provisional application No. 61/398,167, filed on Jun. 22, 2010, provisional application No. 61/398,751, filed on Jun. 30, 2010.

(51) Int. Cl.
| | |
|---|---|
| *A61F 13/00* | (2006.01) |
| *A61F 15/00* | (2006.01) |
| *A61L 15/00* | (2006.01) |
| *A61L 15/16* | (2006.01) |
| *C07K 14/00* | (2006.01) |
| *A61K 35/14* | (2006.01) |
| *A61K 38/18* | (2006.01) |

(52) U.S. Cl. ........ 424/443; 424/445; 424/446; 424/447; 530/350; 530/351; 530/380; 514/8.1; 514/8.2; 514/8.9; 602/42; 602/43; 602/48; 602/50

(58) Field of Classification Search .................... None
See application file for complete search history.

(56) References Cited

U.S. PATENT DOCUMENTS

| | | |
|---|---|---|
| 8,058,066 B2 | 11/2011 | Marshall et al. |
| 8,088,732 B2 | 1/2012 | Marshall et al. |
| 2007/0160653 A1 | 7/2007 | Fischer et al. |
| 2008/0096164 A1 | 4/2008 | Fischer et al. |
| 2009/0053288 A1 | 2/2009 | Eskridge et al. |

OTHER PUBLICATIONS

Steed et al. (2008), ePlasty, vol. 8, pp. 1-6 (E-location ID:e18).*
Ten Breteler, M R., et al., 2002, AUTEX Res J, 2(4):176-189.
Fischer, T.H., et al., 2009, J Biomed Materials Res Part B: Applied Materials, pp. 381-389.
Stasilon(TM) Product Sheet, Entegrion, PO Box 14867, Research Triangle Park, NC, 27709.

* cited by examiner

*Primary Examiner* — Christine J Saoud
*Assistant Examiner* — Jegatheesan Seharaseyon
(74) *Attorney, Agent, or Firm* — Linda O. Palladino; Gail M. Kempler

(57) ABSTRACT

The invention is directed to a wound healing device. Such wound healing device utilizes novel wound healing compositions embedded onto or into a natural plant-derived cloth-based matrix.

6 Claims, No Drawings

WOUND HEALING DEVICE

CROSS-REFERENCE TO RELATED APPLICATIONS

This application claims priority under 35 USC §119(e) of U.S. Provisional Application No. 61/398,167, filed Jun. 22, 2010, and U.S. Provisional Application No. 61/398,751, filed Jun. 30, 2010, the entireties of which are incorporated herein by reference.

FIELD OF THE INVENTION

The field of the invention is directed to a wound healing device. Such wound healing device utilizes novel wound healing compositions embedded onto or into a natural plant-derived cloth-based matrix.

DESCRIPTION OF RELATED ART

STASILON® (Entergrion, Inc., Research Triangle Park, NC) is a novel hemostatic woven textile composed of allergen-free fibers of continuous filament fiberglass and bamboo yarn.

BACKGROUND OF THE INVENTION

Wounds are typically washed with normal saline. A bactericidal treatment may be applied and the wound is then covered with a dressing, typically cotton gauze. This may be suitable for many wounds, but not all. Some wounds bleed proficiently, so a hemostatic agent may be applied to control the bleeding. Other wounds, such as large surface area wounds as may be seen in a motorcycle accident where extensive road abrasion to the skin has occurred, may exhibit significant blood loss merely because of the large surface wound involved, even though the wound itself may be superficial. In these cases, it is desirable to have a dressing which exhibits hemostatic properties. For example, the product Stasilon® is a novel hemostatic woven textile composed of allergen-free fibers of continuous filament fiberglass and bamboo yarn that has such an application. However, in addition to hemostatic properties, it would be desirable to have a dressing that also possesses enhanced wound healing properties.

Many individual cytokines and growth factors have been evaluated for their therapeutic utility in the treatment of many varied diseases, disorders and injuries. Unfortunately, the results have been only partially encouraging. For example, PDGF-BB has proven to be useful in the treatment of diabetic foot ulcers; GM-CSF is marketed in Europe for both venous ulcers and diabetic foot ulcers; and HGH (human growth hormone) is marketed in the US for pediatric burns. Failures include BDNF, CNTF and IGF-1 which have all been evaluated in clinical trials designed to test their efficacy in treating ALS, each with disappointing results; TGFβ2 was unsuccessful in a phase 2 study for venous ulcers; and IGF-1 and PDGF combination therapy was unsuccessful in diabetic foot ulcers.

While is not clear why so many of these individual cytokines and growth factors have failed in the clinic, one theory is that the proteins were being administered in doses that were not physiologic, i.e. very high doses compared to the physiologic levels normally found in vivo. Also, because of the complex interaction between cytokines and growth factors in a given physiological niche, the application of just one factor, especially one at abnormally high levels, cannot be expected to faithfully recreate the physiological niche and may, in fact, grossly disturb its delicate balance.

BRIEF SUMMARY OF THE INVENTION

It is an object of the subject invention to provide a wound healing device which utilizes novel wound healing compositions present at physiologic concentrations that are embedded in a natural cloth-based matrix.

Accordingly, a first aspect of the invention is device comprising a cloth which is embedded with a wound healing composition, wherein the wound healing composition comprises protein factors that are dissolved in an aqueous solution. In one embodiment of the device of aspect one the cloth has the property of hemostatic activity and/or anti-infectious agent activity and/or antibacterial activity.

In another embodiment of the device of aspect one the cloth is made of a natural, plant-derived fiber. In a particular embodiment the plant-derived fiber has a rough surface. In another embodiment, the cloth does not stick to the wound. In another embodiment, the cloth is made of more than one fiber and/or other material (glass, Teflon®, Gor-Tex®, hair, feathers, etc.)

In another embodiment the wound healing composition is selected from the group consisting of Amnion-derived Cellular Cytokine Solution (ACCS) or Physiologic Cytokine Solution (PCS), or a combination thereof. In a specific embodiment the protein factors are VEGF, Angiogenin, PDGF, TGFβ2, TIMP-1 and TIMP-2. In a more specific embodiment the protein factors are at physiologic levels. In a very specific embodiment the physiologic levels are ~5-16 ng/mL for VEGF, ~3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2.

In another embodiment, the device of aspect one has been irradiated to achieve sterility. Another embodiment is a sterile package containing the device of aspect one. Still another embodiment is a kit comprising the device of aspect one and instructions for the use of the device to treat wounds.

Other features and advantages of the invention will be apparent from the accompanying description, examples and the claims. The contents of all references, pending patent applications and issued patents, cited throughout this application are hereby expressly incorporated by reference. In case of conflict, the present specification, including definitions, will control.

DEFINITIONS

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of a cell or cell population. The protein marker may be located on the plasma membrane of a cell or in some cases may be a secreted protein.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "Amnion-derived Multipotent Progenitor cell" or "AMP cell" means a specific population of cells that are epithelial cells derived from the amnion. AMP cells have the following characteristics. They have not been cultured in the presence of any non-human animal materials, making them and cell products derived from them suitable for human clinical use as they are not xeno-contaminated. AMP cells are cultured in basal medium supplemented with human serum albumin. In a preferred embodiment, the AMP cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 μg/mL for TIMP-1 and ~1.04 μg/mL for TIMP-2. The AMP cells may optionally express Thymosin P4. AMP cells grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion-derived cells, from which AMP cells are isolated, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172: 493-500). However, the methods used herein provide improved compositions and populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher yield of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein.

As used herein, the term "Amnion-derived Cellular Cytokine Solution" or "ACCS" means conditioned medium that has been derived from AMP cells or expanded AMP cells that have been cultured in basal media supplemented with human serum albumin. Amnion-derived Cellular Cytokine Solution or ACCS has previously been referred to as "amnion-derived cytokine suspension".

The term "physiological level" as used herein means the level that a substance in a living system is found, for example, in the circulatory system or in a particular microenvironment or biological niche in the living system, and that is relevant to the proper functioning of biochemical and/or biological processes.

As used herein, the term "physiologic cytokine solution" or "PCS" composition means a composition which is not cell-derived and which has physiologic concentrations of one or more factors selected from VEGF, Angiogenin, PDGF and TGFβ2 and at least one MMP inhibitor. Examples of suitable MMP inhibitors include but are not limited to TIMP-1 and TIMP-2.

As used herein, the term "pooled" means a plurality of compositions that have been combined to create a new composition having more constant or consistent characteristics as compared to the non-pooled compositions. For example, pooled ACCS has more constant or consistent characteristics compared to non-pooled ACCS. Examples of pooled compositions include "SP pools" (more than one ACCS collection/one placenta), "MP1 pools" (one ACCS collection/placenta, multiple placentas), and "MP2 pools" (more than one ACCS collection/placenta, multiple placentas).

The term "therapeutically effective amount" means that amount of a therapeutic agent necessary to achieve a desired physiological effect (i.e. treat wounds).

As used herein, the term "pharmaceutically acceptable" means that the components, in addition to the therapeutic agent, comprising the formulation, are suitable for administration to the patient being treated in accordance with the present invention.

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein the term "standard animal model for wound healing" refers to any art-accepted animal model for wound healing in which the compositions of the invention exhibit efficacy as measured by accelerated wound healing. Non-limiting examples of suitable models are described in Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990; DelBecarro, et al: The use of specific thromboxane inhibitors to preserve the dermal microcirculation after burning. Surgery 87: 137-114, 1980; Robson, et al: Increasing dermal perfusion after burning by decreasing thromboxane production. J Trauma 20: 722-725, 1980; Polo, et al: An in vivo model of human proliferative scar. J Surg Res 74: 187-195, 1998.). Skilled artisans are aware of other suitable models.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Uses

Wound Healing

The instant invention is based upon the discovery that AMP cells, ACCS derived therefrom, cell lysates therefrom, cell products derived therefrom, and extracellular matrices therefrom, alone or in combination with each other and/or other agents, including active and non-active agents, can accelerate the wound healing process for all wound types, particularly when administered topically, i.e. to the surface of the wound site, or subcutaneously. Using, AMP cells and ACCS derived from AMP cells, all wound types, mechanical or thermal, acute or chronic, infected or sterile, or congenital, undergo healing more rapidly than similar wounds left to heal naturally or which are treated with currently available methods.

The compositions and methods of the present invention are effective in accelerating wound healing of wounds caused by a number of sources, including but not limited to incisional, compression, thermal, acute, chronic, infected, sterile and congenital injuries.

In addition to accelerating wound healing, the compositions of the invention prevent and/or reduce the incidence of wound failure, such as hernia formation, by increasing both breaking strength and tensile strength of wounds as well as increasing the rate in which increased breaking strength and tensile strength is attained during the wound healing process. Thus, wounds not only heal faster, but become stronger faster than wounds treated with other available agents or untreated.

Importantly, it has been discovered that the AMP cells and ACCS of the invention are able to accelerate the rate of wound healing (including increased wound strength) in both non-contaminated and contaminated (infected) wounds. It is long known in the art that infected wounds either do not heal or the rate of healing is very slow. However, using the novel compositions and methods described herein, Applicants have found that the rate of wound healing is accelerated even when the wound is infected. This unique ability to heal the wounds in the face of infection is not based on any antibacterial effect of the compositions, but rather is due to the unique combination of physiologically relevant cytokines secreted by the cells of the invention at physiological levels. The secretion of these physiologically relevant cytokines may be into the extracellular space in which they are placed or into culture media to form ACCS. Such physiologically relevant cytokines include VEGF, PDGF, Angiogenin, TGFβ2, TIMP-1 and TIMP-2.

These cytokines are known to be involved in many physiological processes including wound healing. VEGF and Angiogenin are both involved in regulating angiogenesis and vascularization. PDGF is involved in regulating cell growth and division and, like VEGF and Angiogenin, plays a significant role in angiogenesis. TGFβ2 is a member of the TGF superfamily, a group of cytokines that play a number of different roles in many cellular functions. TIMP-1 and TIMP-2 are tissue inhibitors of metalloproteinases (MMPs). MMPs are a family of inflammatory cytokines that are present in high levels in non-healing wounds and are thought to interfere with wound healing by destroying cytokines and other proteins essential to the wound healing process. Previous studies have demonstrated that the ratio of MMP-9 to TIMP-1 in wound fluids is inversely correlated with the healing of pressure wounds (Ladwig, GP, et al. Wound Rep Reg 2002, 10:26-37). Applicants have discovered that the physiologically relevant levels of TIMP-1 and TIMP-2 secreted by the cells of the invention, in particular AMP cells, and found in, for example, ACCS, block MMP activity and thus promote accelerated wound healing.

The compositions of the invention are applied in a therapeutically effective amount to accomplish accelerated wound healing, including increased wound strength and decreased wound failure. A "therapeutically effective amount" of a therapeutic agent within the meaning of the present invention will be determined by a patient's attending physician or veterinarian. Such amounts are readily ascertained by one of ordinary skill in the art and will enable accelerated wound healing when administered in accordance with the present invention. Factors which influence what a therapeutically effective amount will be include, the specific activity of the therapeutic agent being used, the wound type (mechanical or thermal, full or partial thickness, etc.), the size of the wound, the wound's depth (if full thickness), the absence or presence of infection, time elapsed since the injury's infliction, and the age, physical condition, existence of other disease states, and nutritional status of the patient. Additionally, other medication the patient may be receiving will affect the determination of the therapeutically effective amount of the therapeutic agent to administer.

Obtaining and Culturing of Cells

AMP cell compositions are prepared using the steps of a) recovery of the amnion from the placenta, b) dissociation of the epithelial cells from the amniotic membrane using a protease, c) culturing of the cells in a basal medium with the addition of a naturally derived or recombinantly produced human protein (i.e. human serum albumin) and no non-human animal protein; d) selecting AMP cells from the epithelial cell culture, and optionally e) further proliferation of the cells, optionally using additional additives and/or growth factors (i.e. recombinant human EGF). Details are contained in US Publication No. 2006-0222634-A1, which is incorporated herein by reference.

Culturing of the AMP cells—The cells are cultured in a basal medium. Such medium includes, but is not limited to, EPILIFE® culture medium for epithelial cells (Cascade Biologicals), OPTI-PRO™ serum-free culture medium, VP-SFM serum-free medium, IMDM highly enriched basal medium, KNOCKOUT™ DMEM low osmolality medium, 293 SFM II defined serum-free medium (all made by Gibco; Invitrogen), HPGM hematopoietic progenitor growth medium, Pro 293S-CDM serum-free medium, Pro 293A-CDM serum-free medium, UltraMDCK™ serum-free medium (all made by Cambrex), STEMLINE® T-cell expansion medium and STEMLINE® II hematopoietic stem cell expansion medium (both made by Sigma-Aldrich), DMEM culture medium, DMEM/F-12 nutrient mixture growth medium (both made by Gibco), Ham's F-12 nutrient mixture growth medium, M199 basal culture medium (both made by Sigma-Aldrich), and other comparable basal media. Such media should either contain human protein or be supplemented with human protein. As used herein a "human protein" is one that is produced naturally or one that is produced using recombinant technology. In specific embodiments, the basal media is IMDM highly enriched basal medium, STEMLINE® T-cell expansion medium or STEMLINE® II hematopoietic stem cell expansion medium, or OPTI-PRO™ serum-free culture medium, or combinations thereof and the human protein is human serum albumin at a concentration of at least 0.5% and up to 10%. In particular embodiments, the human albumin concentration is from about 0.5 to about 2%. In a specific embodiment the human serum albumin is at 0.5%. The human serum albumin may come from a liquid or a dried (powder) form and includes, but is not limited to, recombinant human serum albumin, PLASBUMIN® normal human serum albumin and PLASMANATE® human blood fraction (both made by Talecris Biotherapeutics).

In a most preferred embodiment, the cells are cultured using a system that is free of non-human animal products and substances to avoid xeno-contamination. In this embodiment, the culture medium is IMDM highly enriched basal medium, STEMLINE® T-cell expansion medium or STEMLINE® II hematopoietic stem cell expansion medium, OPTI-PRO™ serum-free culture medium, or DMEM culture medium, with human serum albumin (PLASBUMIN® normal human serum albumin) added up to concentrations of 10%. A particular embodiment is one wherein the human serum albumin is at 0.5%. The invention further contemplates the use of any of the above basal media wherein animal-derived proteins are replaced with recombinant human proteins and animal-derived serum, such as BSA, is replaced with human serum albumin. In preferred embodiments, the media is serum-free in addition to being animal-free.

Optionally, other factors are used. In one embodiment, epidermal growth factor (EGF) at a concentration of between 0-1 µg/mL is used. In a preferred embodiment, the EGF concentration is around 10-20 ng/mL. Alternative growth factors which may be used include, but are not limited to, TGFα or TGFβ2 (5 ng/mL; range 0.1-100 ng/mL), activin A, cholera toxin (preferably at a level of about 0.1 µg/mL; range 0-10 µg/mL), transferrin (5 µg/mL; range 0.1-100 µg/mL), fibroblast growth factors (bFGF 40 ng/mL (range 0-200 ng/mL), aFGF, FGF-4, FGF-8; (all in range 0-200 ng/mL), bone morphogenic proteins (i.e. BMP-4) or other growth factors known to enhance cell proliferation. All supplements are human clinical grade.

In a specific embodiment, the following method is used to obtain selected AMP cells. The cells are plated into plastic tissue culture vessels (i.e. T75 flasks) immediately upon isolation from the amnion. After ~1-5 days, preferably ~1-3 days, and most preferably ~2 days in culture, non-adherent cells are removed from the plastic tissue culture vessel and discarded and the adherent cells are kept. This attachment of cells to a plastic tissue culture vessel is the selection method used to obtain the desired population of AMP cells. Adherent and non-adherent AMP cells appear to have similar cell surface marker expression profiles but the adherent cells have the advantage of possessing greater viability than the non-adherent population of cells and are thus the desired population of AMP cells. Adherent AMP cells are cultured until they reach ~13,000-700,000 cells/cm$^2$, preferably ~53,000-500,000 cells/cm$^2$ and most preferably ~120,000-300,000 cells/cm$^2$. At this point, the cultures are confluent or close to confluent. Suitable cells cultures will reach this number of cells between ~5-14 days, preferably between 5-9 days. Attaining this criterion is an indicator of the proliferative potential of the AMP cells and cells that do not achieve this criterion are not selected for further analysis and use. Once the AMP cells reach ~13,000-700,000 cells/cm$^2$, preferably ~53,000-500,000 cells/cm$^2$ and most preferably ~120,000-300,000 cells/cm$^2$, they are removed from the plastic tissue culture vessel and cryopreserved. This collection time point is called p0.

The AMP cells of the invention are characterized by assaying for secretion of physiologically relevant cytokines and growth factors. Suitable cells are those in which each cytokine or growth factor occurs in the physiological range of ~5.0-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2. The cells may optionally be assayed for Thymosin β4.

Generation of ACCS—The AMP cells of the invention can be used to generate ACCS. In one embodiment, the AMP cells are isolated as described herein and 1×10$^6$ cells/mL are seeded into T75 flasks containing between 5-30 mL culture medium, preferably between 10-25 mL culture medium, and most preferably about 10 mL culture medium. The culture medium is preferably a basal medium (for example IMDM highly enriched basal medium) which is supplemented with human serum albumin. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention. It is also contemplated by the instant invention that the ACCS be cryopreserved following collection. It is also contemplated by the invention that ACCS be lyophilized following collection. It is also contemplated by the invention that ACCS be formulated for sustained-release following collection. It is also contemplated that ACCS production be scaled up for generation of sufficient product for clinical testing and for commercialization. Skilled artisans are familiar with cryopreservation lyophilization, and sustained-release formulation methodologies.

Generation of Physiologic Cytokine Solution (PCS) Compositions

A non-cellular derived form of ACCS (referred to herein as Physiologic Cytokine Solution ("PCS") composition is generated by combining physiological levels of one or more of VEGF, Angiogenin, PDGF, TGFβ2, and one or more MMP inhibitor (i.e. TIMP-1 and/or TIMP-2) in a carrier. Optionally, the PCS contains Thymosinβ4. The physiological levels for these cytokines are the same as those found in ACCS. Suitable carriers include normal saline, PBS, lactated Ringer's solution, cell culture medium, conditioned cell culture media, water, etc. Such compositions are suitable for cryopreservation, lyophilization, sustained-release formulation, scale-up, and the like. It is contemplated by the present invention that PCS may be produced such that it contains more concentrated levels of the factors than those found in ACCS and that it may be subsequently diluted with appropriate diluent prior to use. Appropriate diluents include, without limitation, normal saline, PBS, lactated Ringer's solution, cell culture media, conditioned cell culture media, water, and the like. Such dilutions may be 1:2, 1:3, 1:4, 1:5, 1:10, 1:100, etc. Such dilutions may also be less than 1:2 (i.e. 1:1, 1:0.5, etc.). The appropriate dilution required will be dependent upon the intended use and therefore will need to be empirically determined by the skilled artisan.

The compositions of the invention can be prepared in a variety of ways depending on the intended use of the compositions. For example, a composition useful in practicing the invention may be a liquid comprising an agent of the invention in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Cloth for Use in the Device

The invention utilizes natural cloths which are embedded with a wound healing composition. Suitable cloths are ones which are plant-derived. Desirable features of the cloth include high absorptive capability, such that maximal amounts of wound healing composition (i.e. ACCS or PCS) maybe embedded onto/into it. Alternatively, cloths whose fibers exhibit a rough or pilled surface as opposed to a smooth surface are also desirable. Such a surface has the advantage of having a high surface area for absorption of the wound healing composition (i.e. ACCS or PCS) as well as for release of the wound healing composition. This allows a great delivery of wound healing composition (i.e. ACCS or PCS) per unit area than conventional techniques such as spray gauze soaked in or covering a therapeutic agent.

Other suitable cloths include ones which have the same or similar rough surface to increase surface area, but which have the wound healing composition (i.e. ACCS or PCS) adsorbed to its fiber surface rather than absorbed by the fibers. Such cloths will exhibit a greater surface area for adsorption and release of the wound healing composition (i.e. ACCS or PCS) than smooth surface cloth fibers, thus delivering a greater amount of wound healing composition (i.e. ACCS or PCS) per unit area than smooth surface fibers. One desirable characteristic is one in which the protein components of the wound healing composition (i.e. ACCS or PCS) do not irreversible stick to the fibers or become denatured in any way.

Additional suitable features for the cloth include hemostatic activity such as that exhibited by, for example, Stasilon® or anti-infectious agent activity such as that exhibited by, for example, Cliniweave® (Whitaker Services, UK) or antibacterial activity such as Acticoat (Smith and Nephew). Further desirable features include a cloth which does not stick to the wound.

The invention also contemplates a device wherein the cloth contains more than one material. For example, more than one plant-based natural fiber may be combined to obtain the desirable characteristics. Alternatively, the plant-based natural fiber(s) may be combined with non-plant based materials. Such materials include, but are not limited to, glass fibers, Teflon® (DuPont), Gor-Tex®, feather, hair, and the like.

Treatment Kits

The invention also provides for an article of manufacture comprising packaging material and a the wound healing device of the invention contained within the packaging material, wherein the wound healing device comprises compositions of ACCS or PCS and a plant-derived cloth matrix. The packaging material comprises a label or package insert which indicates that the device can be used for treating wounds.

Administration

One of skill in the art may readily determine the appropriate administration for a particular purpose. The skilled artisan will recognize that a administration is one which produces a therapeutic effect, such as wound healing, in a patient in need thereof Of course, proper doses administration will require empirical determination at time of use based on several variables including but not limited to the severity and type of injury; patient age, weight, sex, health; other medications and treatments being administered to the patient; and the like. One of skill in the art will also recognize that number of administrations (administration regimen) to be administered needs also to be empirically determined based on, for example, severity and type of injury being treated. In a preferred embodiment, one administration is sufficient. Other preferred embodiments contemplate, 2, 3, 4, or more administrations.

The present invention provides a method of treating wound healing by administering to a subject the device in a therapeutically effective amount. By "therapeutically effective amount" is meant the amount of the device administered which is sufficient to elicit a therapeutic effect.

In further embodiments of the present invention, at least one additional agent or treatment modality may be combined with the device. Such agents or treatment modalities may include, for example cytokines, chemokines, antibodies, inhibitors, antibiotics, anti-fungals, anti-virals, immunosuppressive agents, and other cell types.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of AMP Cell Compositions

Recovery of AMP Cells

AMP cells were dissociated from starting amniotic membrane using the dissociation agents PXXIII. The average weight range of an amnion was 18-27 g. The number of cells recovered per g of amnion was about $10\text{-}15 \times 10^6$ for dissociation with PXXIII.

Method of Obtaining Selected AMP Cells

Cells were plated immediately upon isolation from the amnion. After ~2 days in culture non-adherent cells were removed and the adherent cells were kept. This attachment to a plastic tissue culture vessel is the selection method used to obtain the desired population of AMP cells. Adherent and non-adherent AMP cells appear to have a similar cell surface marker expression profile but the adherent cells have greater viability and are the desired population of cells. Adherent AMP cells were cultured in basal medium supplemented with human serum or human serum albumin until they reached ~120,000-150,000 cells/cm². At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reached ~120,000-150, 000 cells/cm², they were collected and cryopreserved. This collection time point is called p0.

Example 2

Generation of ACCS

The AMP cells of the invention can be used to generate ACCS, including pooled ACCS. The AMP cells were isolated as described above and ~1×10⁶ cells/mL were seeded into T75 flasks containing ~10 mL culture medium as described above. The cells were cultured until confluent, the medium was changed and ACCS was collected 3 days post-confluence. Optionally, the ACCS is collected again after 3 days, and optionally again after 3 days. Skilled artisans will recognize that other embodiments for collecting ACCS from confluent cultures, such as using other tissue culture vessels, including but not limited to cell factories, flasks, hollow fibers, or suspension culture apparatus, etc. are also contemplated by the methods of the invention (see Detailed Description above). It is also contemplated by the instant invention that the ACCS be cryopreserved, lyophilized, irradiated or formulated for sustained-release following collection. It is also contemplated that ACCS be collected at different time points (see Detailed Description for details).

Example 3

Generation of Pooled ACCS

ACCS was obtained essentially as described above. In certain embodiments, ACCS was collected multiple times from an AMP cell culture derived from one placenta and these multiple ACCS collections were pooled together. Such pools are referred to as "SP pools" (more than one ACCS collection/one placenta). In another embodiment, AMP cell cultures were derived from several placentas, i.e. from 5 or 10 placentas. The AMP cells from each placenta were cultured and one ACCS collection from each culture was collected and then they were all pooled. These pools are termed "MP1 pools" (one ACCS collection/placenta, multiple placentas). In yet another embodiment, AMP cell cultures were derived from several placentas, i.e. from 5 or 10 placentas. The AMP cells from each placenta were cultured and more than one ACCS collection was performed from each AMP cell culture and then pooled. These pools are termed "MP2 pools" (more than one ACCS collection/placenta, multiple placentas).

Example 4

Generation of PCS Compositions

The following PCS compositions are produced by combining the indicated cytokine or factor at physiologic levels in a carrier:

Composition A: VEGF and TIMP-1
Composition B: VEGF, Angiogenin and TIMP-1
Composition C: VEGF, Angiogenin, PDGF-BB and TIMP-1
Composition D: VEGF, Angiogenin, PDGF-BB, TGFβ2 and TIMP-1
Composition E: VEGF and TIMP-2
Composition F: VEGF, Angiogenin and TIMP-2
Composition G: VEGF, Angiogenin, PDGF-BB and TIMP-2
Composition H: VEGF, Angiogenin, PDGF-BB, TGFβ2 and TIMP-2

Composition I: VEGF, TIMP-1 and TIMP-2
Composition J: VEGF, Angiogenin, TIMP-1 and TIMP-2
Composition K: VEGF, Angiogenin, PDGF-BB, TIMP-1 and TIMP-2
Composition L: VEGF, Angiogenin, PDGF-BB, TGFβ2, TIMP-1 and TIMP-2
Composition M: Angiogenin and TIMP-1
Composition N: Angiogenin, PDGF-BB and TIMP-1
Composition O: Angiogenin, PDGF-BB, TGFβ2 and TIMP-1
Composition P: Angiogenin and TIMP-2
Composition Q: Angiogenin, PDGF-BB and TIMP-2
Composition R: Angiogenin, PDGF-BB, TGFβ2 and TIMP-2
Composition S: Angiogenin, PDGF-BB, TGFβ2, TIMP-1 and TIMP-2
Composition T: PDGF-BB and TIMP-1
Composition U: PDGF-BB, TGFβ2 and TIMP-1
Composition V: PDGF-BB and TIMP-2
Composition W: PDGF-BB, TGFβ2 and TIMP-2
Composition X: PDGF-BB, TIMP-1 and TIMP-2
Composition Y: PDGF-BB, TGFβ2, TIMP-1 and TIMP-2

Compositions A-Y optionally contains Thymosin β4. Skilled artisans will recognize that in certain embodiments other MMP inhibitors (i.e. TIMP-3, TIMP-4 or synthetic MMP inhibitors) may be suitable (J. Frederick Woessner, Jr., J. Clin. Invest. 108(6): 799-800 (2001); Brew, K., et al, Biochim Biophys Acta. 2000 Mar. 7; 1477(1-2):267-83).

VEGF, Angiogenin, PDGF-BB, TGFβ2, TIMP-1 and TIMP-2 are added at the following physiologic levels: ~5-16 ng/mL for VEGF, ~3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2. VEGF may be obtained from Invitrogen, catalog #PHG0144, PHG0145, PHG0146, PHG0141 or PHG0143; Angiogenin may be obtained from R&D Systems, catalog #265-AN-050 or 265-AN-250; PDGF-BB may be obtained from Invitrogen, catalog #PHG0044, #PHG0045, #PHG0046, #PHG0041, #PHG0043; TGFβ2 may be obtained from Invitrogen, catalog #PHG9114; TIMP-1 may be obtained from R&D Systems, catalog #970-TM-010; and TIMP-2 may be obtained from R&D Systems, catalog #971-TM-010. VEGF, Angiogenin, PDGF-BB, TGFβ2, TIMP-1 and TIMP-2 are added to a carrier such as normal saline, PBS, lactated Ringer's solution, cell culture media, water or other suitable aqueous solutions known to skilled artisans.

Example 5

Generation of the Wound Healing Device and Testing in an Animal Model of Wound Healing Suitable cloths having the features described above are submerged in either ACCS or PCS (each of which are prepared as described above) until saturated. The size of the cloth is determined empirically based on the surface area of wound to be treated. Preferably, the cloth should cover the entire wound surface. The Wound Healing Device is then tested in an art-accepted animal model of wound healing (see, for example, Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990; DelBecarro, et al: The use of specific thromboxane inhibitors to preserve the dermal microcirculation after burning. Surgery 87: 137-141, 1980; Robson, et al: Increasing dermal perfusion after burning by decreasing thromboxane production. J Trauma 20: 722-725, 1980; Polo, et al: An in vivo model of human proliferative scar. J Surg Res 74: 187-195, 1998.). Skilled artisans are aware of other suitable models.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A skin wound healing device for topical administration comprising a cloth which is embedded with a wound healing composition, wherein the skin wound healing composition comprises protein factors selected from the group consisting of physiologic levels of VEGF, Angiogenin, PDGF, TGFβ2, TIMP-1 and TIMP-2 that are dissolved in an aqueous solution, wherein the physiologic levels are ~5-16 ng/mL for VEGF, ~3.5-4.5 ng/mL for Angiogenin, ~100-165 pg/mL for PDGF, ~2.5-2.7 ng/mL for TGFβ2, ~0.68 μg mL for TIMP-1 and ~1.04 μg/mL for TIMP-2.

2. The skin wound healing device of claim 1 wherein the cloth has the property of hemostatic activity and/or anti-infectious agent and/or antibacterial activity.

3. The skin wound healing device of claim 1 wherein the cloth is made of a natural, plant-derived fiber.

4. The skin wound healing device of claim 3 wherein the plant-derived fiber has a rough surface.

5. The skin wound healing device of claim 1 which has been irradiated to achieve sterility.

6. The skin wound healing device of claim 1 which is contained in a sterile package.

* * * * *